(12) United States Patent
Kourtakis et al.

(10) Patent No.: US 6,903,047 B2
(45) Date of Patent: Jun. 7, 2005

(54) VANADIUM-PHOSPHORUS OXIDE CATALYSTS WITH PROMOTER REAGENTS

(75) Inventors: Kostantinos Kourtakis, Media, PA (US); Pratibha Laxman Gai, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 3 days.

(21) Appl. No.: 10/169,676

(22) PCT Filed: Jan. 16, 2001

(86) PCT No.: PCT/US01/01422

§ 371 (c)(1),
(2), (4) Date: Jul. 1, 2002

(87) PCT Pub. No.: WO01/52983

PCT Pub. Date: Jul. 26, 2001

(65) Prior Publication Data

US 2003/0036475 A1 Feb. 20, 2003

Related U.S. Application Data

(60) Provisional application No. 60/177,134, filed on Jan. 20, 2000.

(51) Int. Cl.$^7$ ............... B01J 27/198; B01J 27/188; B01J 23/00; B01J 27/182
(52) U.S. Cl. ............... 502/209; 502/210; 502/211; 502/212; 502/213; 502/214; 502/305; 502/308; 502/309; 502/310; 502/311; 502/312; 502/313; 502/314; 502/315; 502/316
(58) Field of Search ............... 502/209–214, 502/305, 308–316

(56) References Cited

U.S. PATENT DOCUMENTS 3,864,280 A    2/1975   Schneider
3,912,763 A  * 10/1975  Farha, Jr. et al. ..... 260/346.1 R
3,985,775 A    10/1976  Harrison
4,132,670 A     1/1979  Katsumoto et al.
4,151,116 A  *  4/1979  McDermott ................. 252/435
4,244,878 A  *  1/1981  McDermott ........... 260/346.75
4,403,943 A     9/1983  Stella
4,410,752 A  * 10/1983  Blum et al. ................. 585/658
4,442,226 A     4/1984  Bither, Jr.
5,011,945 A  *  4/1991  Taheri ........................ 549/260
5,095,125 A  *  3/1992  Haddad et al. ............. 549/259
5,158,923 A  * 10/1992  Barone ....................... 502/209
5,296,436 A  *  3/1994  Bortinger .................... 502/209
5,543,532 A     8/1996  Kourtakis et al.
5,922,637 A  *  7/1999  Bortinger .................... 502/209
5,945,368 A  *  8/1999  Felthouse et al. ........... 502/209
6,048,987 A  *  4/2000  Groke et al. ................ 549/260
6,107,234 A  *  8/2000  Bortinger .................... 502/209
2002/0161243 A1 * 10/2002 Zehner et al. .............. 549/262

OTHER PUBLICATIONS

Hutchings, Graham J., Effect of promoters and reactant concentration on the selective oxidation of n–butane to maleic anhydride using vanadium phosphorus oxide catalysts, Applied Catalysis, pp. 1–32, B.V. Amsterdam, Sep. 1990.

* cited by examiner

*Primary Examiner*—Mark L. Bell
*Assistant Examiner*—Patricia L. Hailey

(57) ABSTRACT

The present invention concerns a method for enhancing the activity of vanadium phosphorus oxide (VPO) catalysts. Promoter reagents are grafted onto or reacted with the catalyst surface. An optional calcination and activation heating cycle transforms the catalyst precursor into a final active phase. A preferred VPO catalyst produced has a ratio of molybdenum to vanadium on the surface of the catalyst to molybdenum to vanadium in the overall bulk of the catalyst represented by the equation (Mo/V) Surface $\geq$ 1.10 (Mo/V) overall bulk.

10 Claims, 7 Drawing Sheets

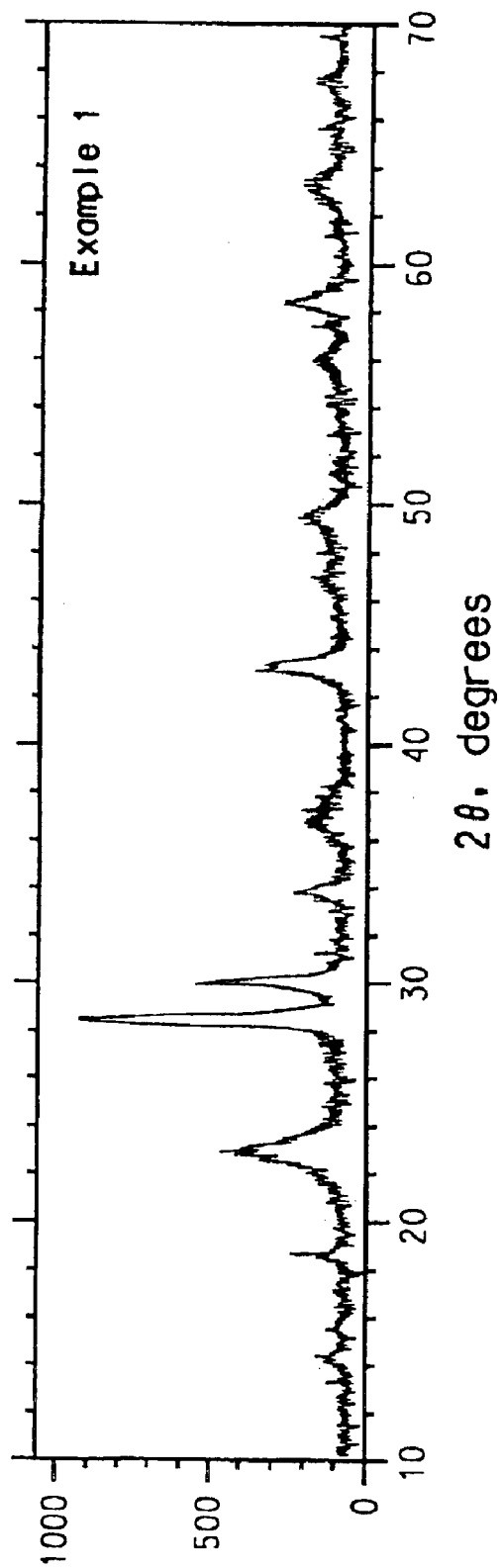

VANADIUM-PHOSPHORUS OXIDE CATALYSTS WITH PROMOTER REAGENTS

This application claims the benefit of provisional application Ser. No. 60/177,134 filed on Jan. 20, 2000.

FIELD OF THE INVENTION

The present invention concerns a method for enhancing the activity of vanadium phosphorus oxide (VPO) catalysts by grafting or otherwise reacting promoter reagents with a catalyst, which may optionally be heated to activate it or may be activated under other reaction conditions, and the catalysts produced by said method.

TECHNICAL BACKGROUND

Commonly held U.S. Pat. No. 5,543,532, hereby fully incorporated by reference, discloses cation substituted VPO catalysts, preferably in the form of solid solutions, which are useful as catalysts for the oxidation of alkane hydrocarbons.

A review of the improvements made in this technology is given by G. J. Hutchings, *Applied Catalysis*, 72 (1991), Elsevier Science Publishers B. V. Amsterdam, pages 1–31. The preferred method of preparation of VPO catalysts is the hydrochloric acid digestion of $V_2O_5$ and $H_3PO_4$ in either an aqueous solvent, as described, for example, in U.S. Pat. No. 3,985,775, or non-aqueous solvent, such as methanol, tetrahydrofuran (THF) or isobutanol, followed by solvent removal to give what is termed the catalyst precursor, vanadium hydrogen phosphate, $VO(HOPO_4) \cdot (H_2O)_{0.5}$.

The precursor is then activated by heating, as described, for example, in U.S. Pat. No. 3,864,280 and U.S. Pat. No. 4,043,943. Further optimization of the preparation is described in U.S. Pat. No. 4,132,670, whereby vanadium pentoxide is heated with a selected anhydrous unsubstituted alcohol, adding an orthophosphoric acid to form the catalyst precursor and calcining the precursor to obtain the catalyst having high intrinsic surface area. Further attempts to improve the VPO catalyst performance by the use of dopants and/or supports are described in U.S. Pat. No. 4,442,226 and U.S. Pat. No. 4,778,890.

Vanadium, phosphorus reagents and oxygen can form a large number of distinct compounds which have been well characterized, e.g., alpha-$VOPO_4$, gamma-$VOPO_4$, $VOHPO_4$, $(VO)_2P_2O_7$, $VO(PO_3)_2$ and $VO(H_2PO_4)_2$. The most active catalytic phase is believed to be $(VO)_2P_2O_7$, which is also the predominant oxide phase in VPO catalysts. Nevertheless, VPO catalysts are usually referred to as "mixed oxides" in recognition of the probable presence of other oxide phases. VPO catalysts typically have V:P atomic ratios in the range of 1:1 to 1:2 and have an average bulk vanadium oxidation state in the range of 4.0–4.3.

G. J. Hutchings and R. Higgins disclose in J. Catalysis 162, 153–168 (1996) methods whereby hydrate salts were physically deposited by incipient wetness onto vanadium hydrogen phosphate precursor. However, there is no distinction made between aqueous and non-aqueous impregnations, nor is reactive grafting discussed. The present invention has found very large differences in examples where nitrate salts and ammonium molybdate (in water) are used versus examples in which alkoxides (in non-aqueous solvents) are used. The differences are apparent both in the differences in reactivity toward hydrocarbon reactants (e.g., n-butane) and in the microstructure of the catalyst.

SUMMARY OF THE INVENTION

The invention concerns a method for enhancing the activity of vanadium phosphorus oxide (VPO) catalysts comprising grafting onto or otherwise reacting a promoter reagent with a catalyst to produce a catalyst composition with a promoter rich surface and wherein said composition is optionally exposed to a heating cycle, which acts to transform the catalyst precursor into a final active phase. Also disclosed is the enhanced catalyst composition produced by said method and a process of using the enhanced catalyst. The enhanced catalyst product has a promoter rich surface. The preferred promoter is molybdenum. Preferably, the relationship of molybdenum to vanadium on the surface of the catalyst to molybdenum to vanadium in the overall bulk of the catalyst is represented by the equation (Mo/V) Surface $\geq 1.10$(Mo/V) overall bulk.

Promoters herein are selected from the group consisting of Mo, Mn, Zn, N, Sn, Fe, Co, T, Zr, Bi, Al, Ti, Cu, Sb or combinations thereof. A preferred promoter is Mo or Mo in combination with one or more of Mn, Zn, N, Sn, Fe, Co, T, Zr, Bi, Al, Ti, Cu, Sb wherein the relationship of Mo and other promoters (represented by A) to the VPO catalyst is shown by the formula $[Mo_{1-x}A_x]_yD$ wherein $0 \leq x \leq 1$ and $0.001 \leq y \leq 0.4$ and wherein D represents vanadium, vanadium phosphorus oxide catalyst or vanadium phosphorus oxide catalyst with binder included therein.

BRIEF DESCRIPTION OF THE DRAWINGS

FIG. 2(*b*) shows the compositional depth profile for an aqueous impregnated catalyst, as described in Comparative Example C. The Mo/V ratio is plotted as a function of the depth of the crystal. In this case, the Mo/V ratio does not vary as a function of depth in the catalyst crystal (vanadium is present uniformly throughout the crystal), indicating that there is no enrichment of molybdenum at or near the crystal surface. This is in marked contrast with Example 1 of this invention, as shown in FIG. 2(*a*).

FIG. 2(*c*) shows the compositional depth profile for an aqueous impregnated catalyst, as described in Comparative Example C. In this case, the Mo/Bi ratio is plotted, and shows that this does not vary from approximately one as a function of depth in the crystal. This is in contrast with Example 1 of the present invention, whose depth profile (Mo/Bi ratio) is shown in FIG. 1, plot A.

DETAILS OF THE INVENTION

Figure 1:
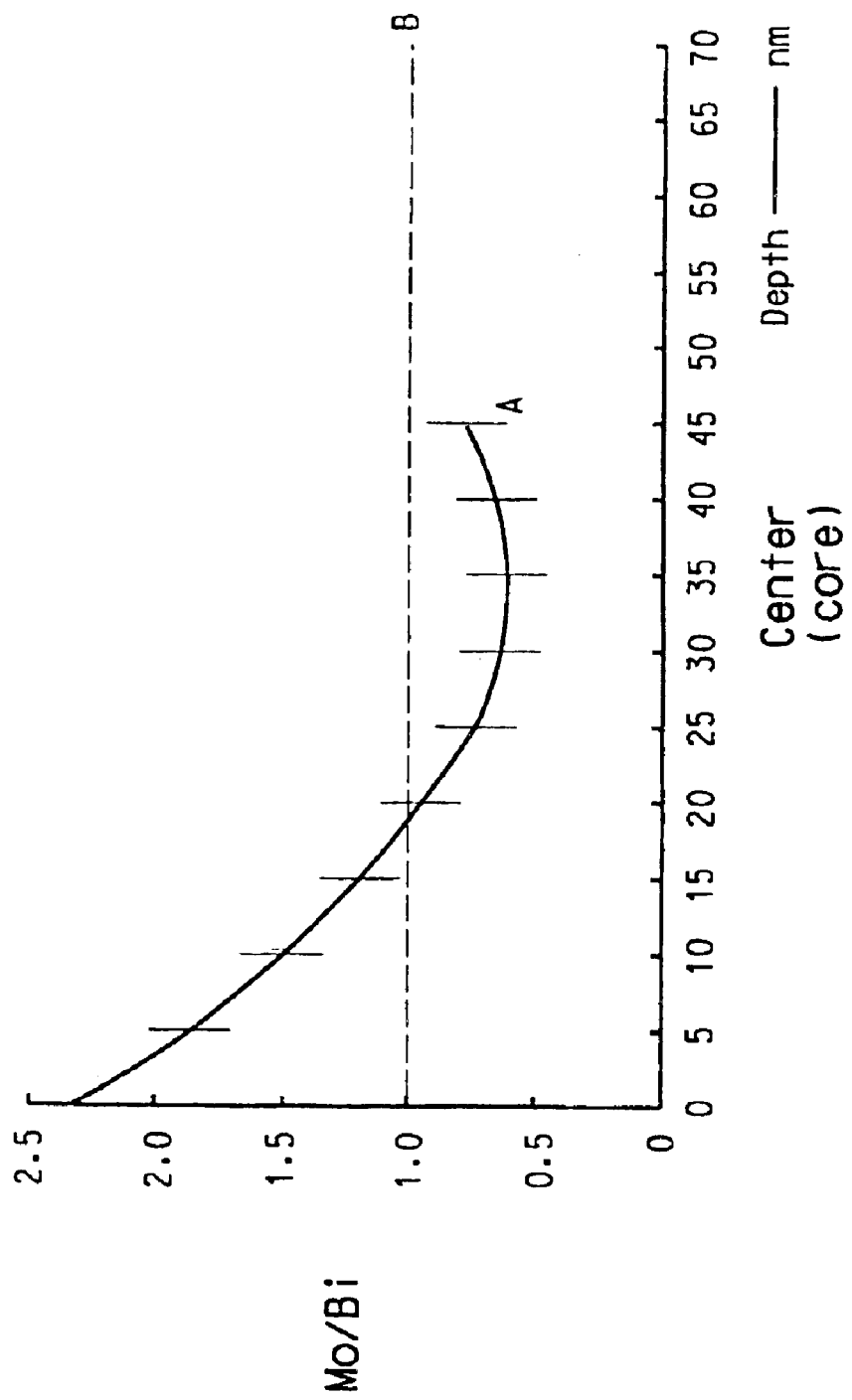
FIG. 1 represents the compositional depth profile of the Mo/Bi ratio as a function of depth in the crystal (from the surface to the core or interior) of cross sectioned catalyst crystals. Plot A is for 1 mole % Bi, Mo VPO catalyst which was prepared by a grafting procedure (Example 1), and plot B is for $(V_{0.9}Bi_{0.05}Mo_{0.05}O)_2P_2O_7$ catalyst prepared by a co-precipitation method, as described in U.S. Pat. No. 5,543,532. Plot A shows enrichment of Mo, relative to bismuth, near the surface of the crystal for the catalyst described in Example 1. For Plot B, Mo/Bi is approximately one and is uniform through the crystal depth, which is markedly different from the profile in the present invention (as shown in FIG. 1, plot A).

The use of the family of vanadium phosphate catalysts, for the oxidation of n-butane to maleic anhydride, is well known in the art. As disclosed in U.S. Pat. No. 5,543,532, VPO catalysts can have various forms. Maleic anhydride is used as a raw material for products ranging from agricultural chemicals, paints, paper sizing and food additives to synthetic resins so that its efficient manufacture is important. While currently used VPO catalysts perform adequately, more efficient catalysts (i.e., those with higher activity and high selectivity) are needed to increase production and provide improved materials.

The current invention concerns a method by which preformed VPO precursors are treated with reagents which serve as promotors, alcohol soluble alkoxide complexes, and are optionally treated by calcination and additional activation. The catalysts formed show superior performance, when compared with untreated catalysts. Reagents which find use in this invention include any moiety which is specifically reactive towards functional groups (e.g., surface hydroxyl and hemihydrate species) on the catalyst surface, including but not limited to alcohol soluble metal alkoxide complexes, anhydrous metal chlorides dissolved in a non-reactive solvent such as carbon tetrachloride (e.g., $MoCl_5$ in $CCl_4$), metal carbonyls dissolved in benzene (e.g., $Mo(CO)_6$ in $C_6H_6$, and other organometallic complexes.

In one embodiment of this invention, bismuth and molybdenum chloride, when reacted with ethanol (EtOH), form a soluble mixed alkoxide complex. The bismuth alkoxide is insoluble in the absence of the molybdenum species, suggesting that a new soluble alcohol complex has been formed containing both bismuth and molybdenum. The alcohol soluble mixed alkoxides is reacted by contacting a solution of these alkoxides at "incipient wetness" on the pre-formed VPO precursor. The VPO precursor is synthesized as described in U.S. Pat. No. 3,864,280. Optionally, it may be processed by spray drying (spray drying of VPO precursor is described in commonly assigned U.S. Pat. Nos. 4,769,477 and 5,543,532, both hereby incorporated by reference). The precursor can also be spray dried with a binder such as silica. As shown in the examples below, these catalysts contain only about 1 mole percent bismuth and molybdenum supported on the commercial precursor synthesized by the method, as disclosed in U.S. Pat. No. 3,864,280, hereby incorporated by reference. Following the impregnation, a standard commercial 460° C. calcination/activation in 1.5% butane/air is used to produce the surface promoted oxides and phosphates on crystalline $(VO)_2P_2O_7$.

The activity of the catalysts produced by the present inventive method, as measured by microreactor testing, as described herein depending upon the composition, is shown to be between about 60% and 250% greater than that of the untreated catalyst, or a catalyst treated with alcohol only, with similar selectivities to maleic anhydride in 2% butane/air.

The surface promoter grafting system of the present invention is an improvement over that described in U.S. Pat. No. 5,543,532, where the VPO catalysts include a bismuth/molybdenum promoter which is prepared by coprecipitating the promoter cations with the vanadium phosphate precursor during precursor synthesis.

The present novel synthetic procedure for supporting the promoters may be implemented by using a combinatorial approach for the rapid synthesis of promoted vanadium phosphorus oxides. If this method were used, a number of promoter grafted catalyst precursors can be produced at one time by robotic delivery of the desired promoter solutions to the catalyst precursors, followed by the calcination and activation steps.

The VPO catalysts, as disclosed in the present invention, may also comprise additional promoter ions. This is expressed by the formula $[Mo_{1-x}A_x]_yD$, wherein A is selected from the group consisting of Mn, Zn, Ni, Sn, Fe, Co, Ti, Zr, Bi, Al, Cu, Sb or combinations thereof; where $0 \leq x \leq 1$ and $0.001 \leq y \leq 0.4$, preferably $0 \leq x \leq 0.75$ and $0.01 \leq y \leq 0.05$; and D represents vanadium, vanadium phosphorus oxide catalyst or vanadium phosphorus oxide catalyst with binder included therein. A preferred binder is $SiO_2$.

Microreactor Evaluations in 2% Butane/Air

Reactor data was obtained in a microreactor facility, disclosed in co-pending and commonly held U.S. patent application Ser. No. 269,211, hereby incorporated by reference, and summarized below in Catalyst Preparation and Evaluations. In the Examples below, an apparent first order rate constant was calculated by varying the volumetric flow rate of gas and contact times. The apparent first order rate constant, k, given for the disappearance of butane, was obtained by fitting the reactor data to a classical first order rate expression:

$$d[butane]/dt = -k[butane]$$

$$d(x_o-x)/dt = -k(x_o-x)$$

where $x_o$=initial concentration of butane
x=portion of butane reacted.

The conversion of butane was based on the difference in the moles between the feed and the products. Selectivity to maleic anhydride was based on butane conversion. The yield is defined as "selectivity times conversion".

Catalyst Preparation and Evaluations

A series of catalysts were prepared to determine the effect of bismuth to molybdenum ratio and promoter loading on catalyst performance. The data are shown in TABLE 1. The evaluation protocol is described in U.S. patent application Ser. No. 269,211.

Prior to their use in the microreactor, the catalysts described herein are typically formed into a convenient catalyst shape by pelletizing the catalyst at about 30,000 psi ($2.07 \times 10^6$ kPa) or less, to form small disks and crushing the pellet through sieves. For fixed bed reactor evaluations, typically a −40, +60 mesh is used (U.S. Sieve Series). Optionally, one could blend the resultant powder with 1–3% of a die lubricant and pellet binder, such as graphite or Sterotex®, a hydrogenated cottonseed oil, commercially available from Capital City Products Company, Columbus, Ohio, before tabletting. For fluidized bed reactor use, the preferred size range is 20 to 150 micrometers.

The catalysts were pelletized at $1.38 \times 10^6$ kPa into disks and subsequently crushed and sieved through (−40, +60) mesh screens. Approximately 0.9 cc of catalyst were used for each evaluation.

The catalyst testing facility consisted of six microreactors which were connected to a common feed source and a common analytical gas chromatograph (GC). Each of the micro-reactors consisted of a 5.0 cm by 0.64 cm stainless steel tube which was immersed in an individual sandbath to maintain isothermal conditions. The feed composition and individual reactor flow rates were metered by commercially available mass flow controllers (Tylan Model FC-260, available from Tylan Corp., Torrance, Calif.). All exit gas lines were heated to 200° C. and connected to a multiport Valco valve for the on-line analysis of products using a commercially available GC (Hewlett-Packard 5890 Series II, Hewlett-Packard, Palo Alto, Calif.). A computer program controlled the Valco valve to select a reactor or feed stream to fill the 0.5 ml sample loop for injection in the GC. The GC was used to analyze for butane, maleic anhydride, acetic acid, acrylic acid, other $C_1$ to $C_4$ hydrocarbons, oxygen, carbon monoxide, carbon dioxide, nitrogen and water.

The standard testing protocol for butane oxidation catalysts was developed to measure maleic anhydride selectivities and yields under hydrocarbon-lean conditions (2% n-butane, 20% oxygen) over a range of butane conversions. The first protocol listed uses a gas feed of 2% butane/air, as described above. The selectivity tabulated is at 40% butane conversion. In this series of experiments, reaction temperature was not varied. For this protocol, the apparent first order rate constant "k" for the disappearance of butane is tabulated, along with the selectivity to maleic anhydride at 40% conversion of butane.

At lower promoter levels of 1 mole percent, a catalyst prepared by grafting molybdenum alkoxide on the vanadium phosphorus oxide precursor showed improved performance for the level of promoter described. This is in contrast to catalysts prepared by the coprecipitation method as disclosed in U.S. Pat. No. 5,543,532.

Aqueous based precursor systems, derived from dissolving bismuth nitrate and ammonium molybdate in water, followed by a similar impregnation procedure onto preformed vanadium phosphate precursors, do not improve the catalysts. See Comparative Example "C" compared to Comparative Example "A". The comparative data shows no improvement in k (sec-1), the first order rate constant (indication of activity).

Other trends in this reactor data are evident by increasing the catalyst loading from 1 mole % Bi, 1 mole % Mo to 2.5 mole % and 5 mole % Bi, 5 mole % Mo. See Examples 1, 3 and 10. An optimum of k=1.61, selectivity=83% is reached near 2.5 mole % Bi, 2.5 mole % Mo. However, 1 mole % Bi and 1 mole % Mo also show nearly a 100% improvement in activity over the Comparative Example A' while maintaining high selectivity to maleic anhydride at 40% conversion of butane. Comparative Examples B and C show that treating VPO precursor with ethanol or HCl in ethanol or water does not show any benefit compared to Comparative Example A'. At least a small amount of the Mo complex must be present to provide solubility of the bismuth complex in ethanol. Example 8 shows that Mo as a grafted promoter gives greater than 100% increase in rate (k ($sec^{-1}$)).

Figure 4A:
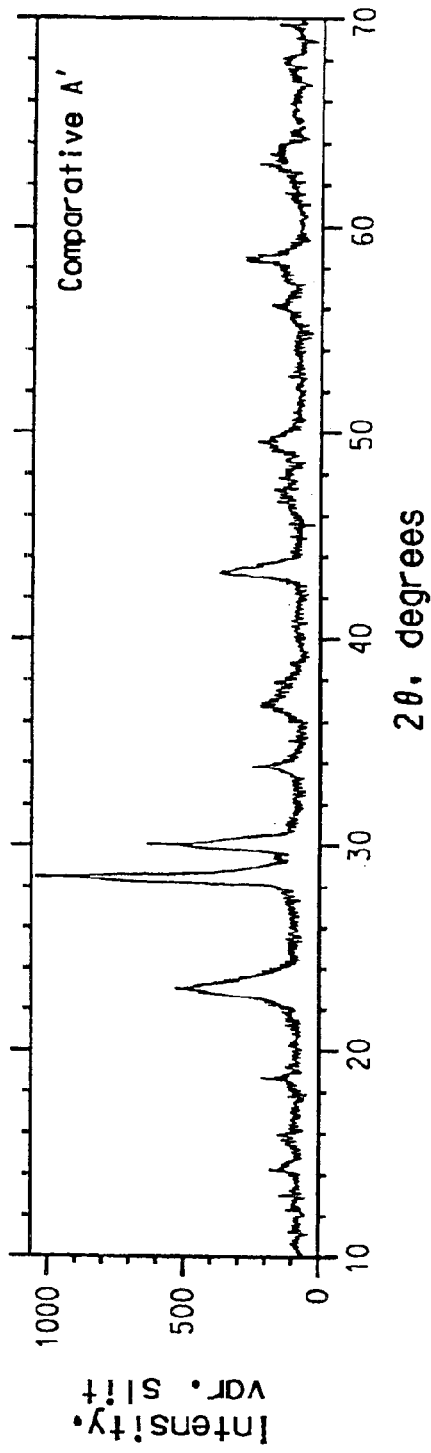
FIGS. 4(a, b and c) shows Powder X-ray Diffraction patterns for Comparative Examples A and A' and for Example 1.
Figure 4B:
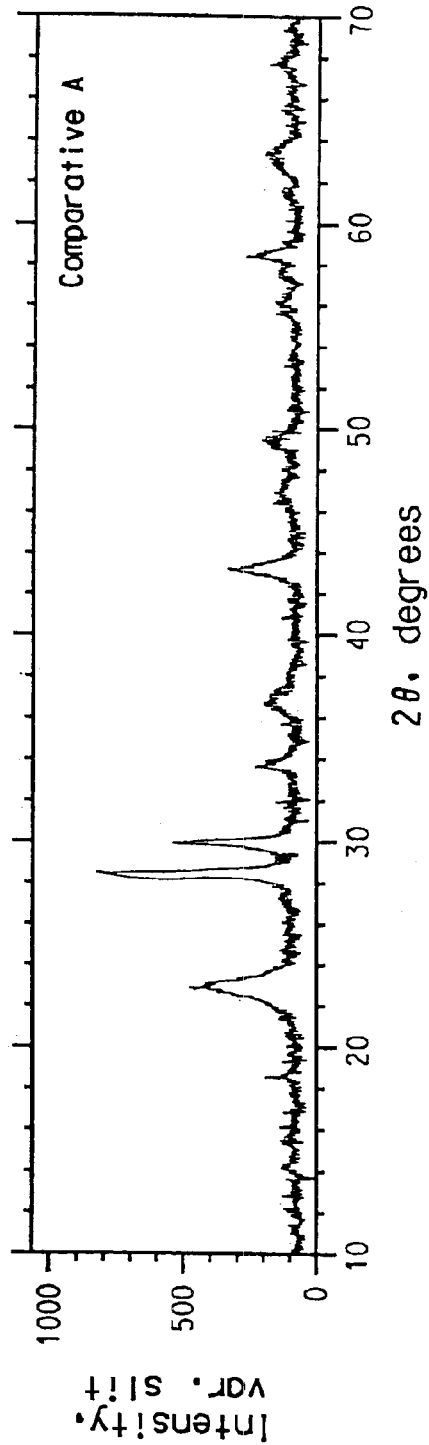

Catalyst Characterization:
Powder X-Ray Diffraction:

Powder x-ray diffraction analysis shows the promoter grafted catalysts to be essentially crystalline (see FIG. 4).

Microstructure and Chemical Composition Analyses: Depth Profiling:
Electron Microscopy (EM) Procedures:

To analyze the microstructure, morphology and chemical composition of the catalysts, a combination of scanning transmission electron microscopy (STEM), high resolution transmission EM (HREM) with atomic resolution and high resolution low voltage scanning EM (LVSEM) were used. These methods are described below.

Catalyst samples prepared with promoter reagents grafted and with the standard co-precipitation method were examined both in plane view, and in cross section to access both the surface and the interior (bulk) of the catalyst particles. For depth profiling, cross sectioned samples were prepared by standard procedures, using epoxy resin to hold catalyst particles and carefully cross-sectioning them using a diamond knife.

High precision chemical compositional analyses were carried out on cross sectioned samples by electron stimulated energy dispersive X-ray compositional spectroscopy (EDX), using advanced instrumentation to provide high spatial resolution (on the (sub) nanometer scale) and chemical composition from localized regions of the particles as follows. The analyses were carried out using a commercial Vacuum-Generators (VG) field emission-gun HB501-STEM and the data were confirmed by using advanced Philips CM200 field emission gun HREM/STEM instrument. Additionally, catalyst microstructural investigations on the atomic scale were performed using a modified Philips CM30 environmental-HREM (EHREM) (as described in P. L. Gai, DuPont: published in Advanced Materials, Vol 10, p. 1259, 1998, hereby incorporated in its entirety) and a Philips CM20 HREM. All the EMs were equipped with X-ray spectrometers to analyze chemical composition.

For compositional profile, the analyses were first carried out from the surface of the particles. The electron nanoprobe was then moved gradually to the center (core) of the particles. Analyses were recorded from many dozens of crystals. For quantitative chemical microanalysis, a ratio method was used given by:

$$C(a)/C(b) = \text{constant factor } (I(a))/I(b),$$

where, C(a) and C(b) are concentrations of the elements a and b, and I(a) and I(b) are the background subtracted peak intensities of (a) and (b) in the X-ray spectrum, using the procedures described by Cliff, G. and Lorimer G. W., J. Microscopy, vol. 103, p. 203. 1975, hereby incorporated in its entirety. The analyses were calibrated using a standard of single phase $Bi_2MoO_6$ compound. Mo/V composition depth profiles were plotted from the surface to the center (core) of the catalyst particles.

Complementary experiments on microstructure and microchemistry of the catalysts were also performed using a Hitachi high resolution S5000 LVSEM as described in E. D. Boyes, DuPont: published in Adv. Materials, Vol. 10, p. 1277, 1998, hereby incorporated in its entirety. In plan view, surface and bulk composition analyses analysis was carried out at different electron accelerating voltages in LVSEM to access the surface and the bulk of the catalyst particles. Microstructures and surface topography of the catalyst particles were recorded.

Figure 2A:
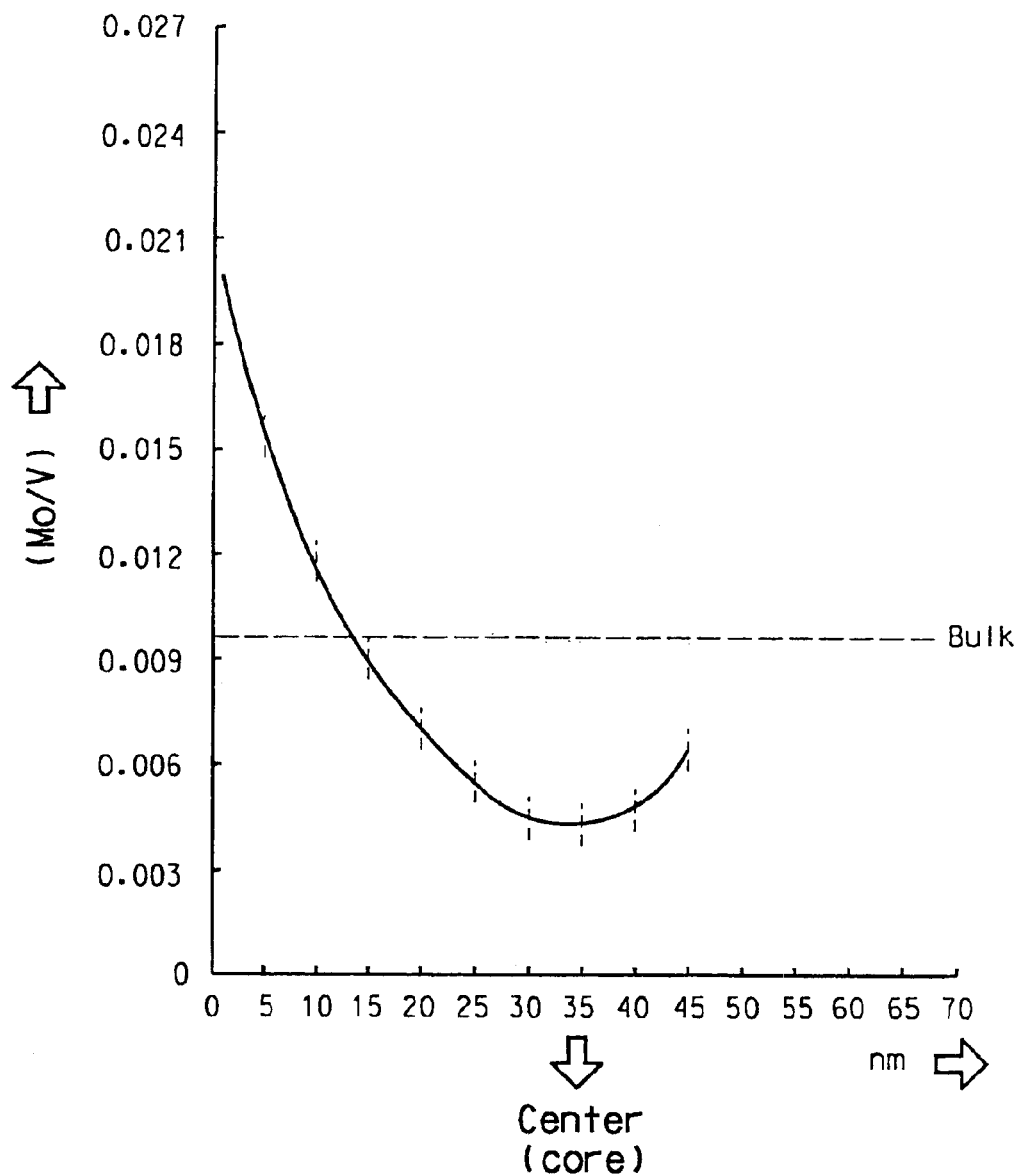
FIG. 2(*a*) shows the compositional depth profile of Example 1. In this case, the ratio of Mo/V is plotted as a function of the depth in the crystal. This shows enrichment of molybdenum, relative to vanadium at and near the surface of the crystal; the vanadium is present uniformly throughout the crystal. Note that the bulk or average composition of the entire crystal is 1 mole % Bi and 1 mole % Mo in VPO (vanadium phosphorus oxide), so that the bulk composition (averaged throughout the entire crystal) ratio is Mo/V=0.01.
Figure 2B:
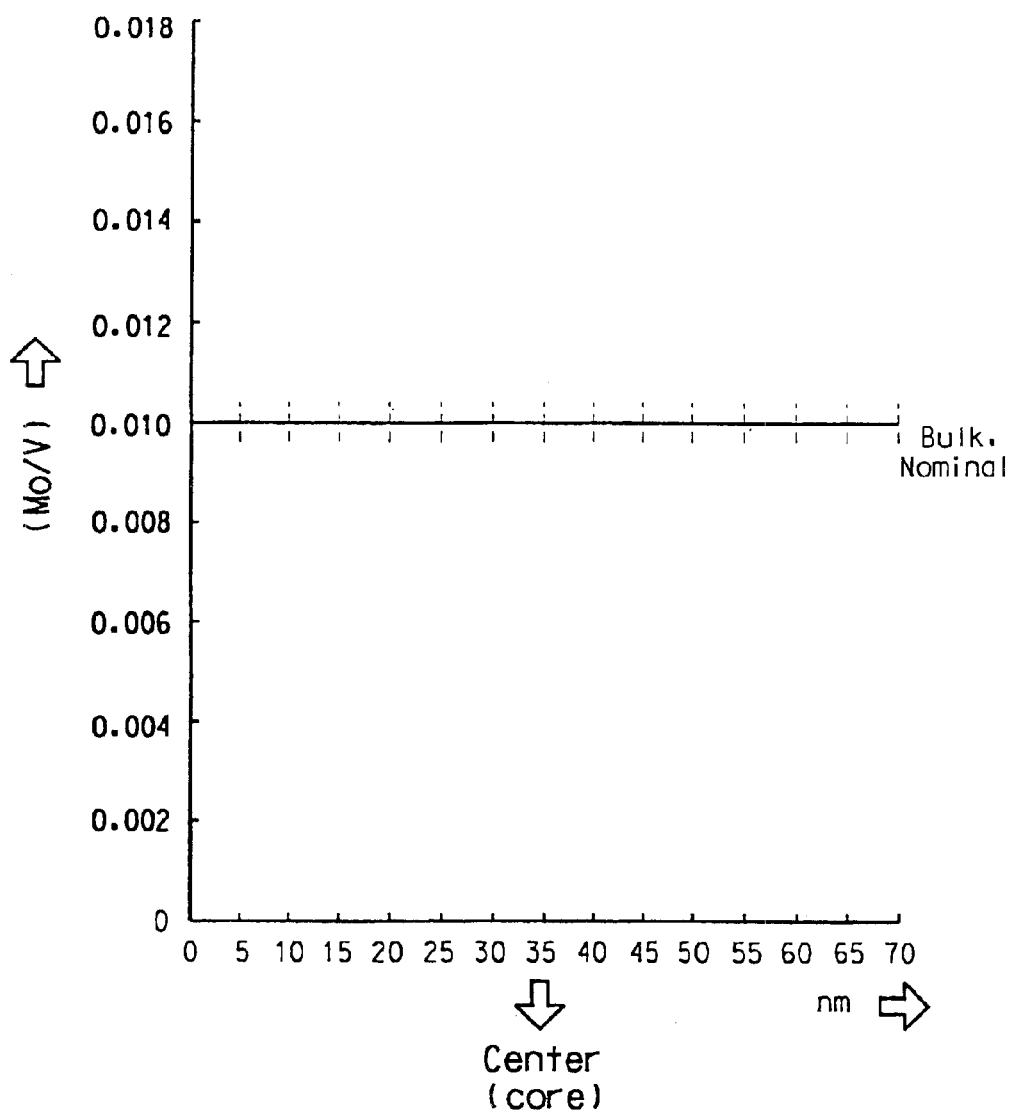

The changes in the depth profile distribution of catalyst composition are not accompanied by changes in surface area, as measured by $N_2$/BET. The presence of the Mo-rich phase is therefore significant. This is shown in FIG. 1, plot A and in FIG. 2A. This is further supported by the observation that catalysts prepared by coprecipitation of the promoter cations (See FIG. 1b) with the vanadium phosphate precursor during precursor synthesis did not show a similar enrichment of Mo on the catalyst surface.

Figure 2C:
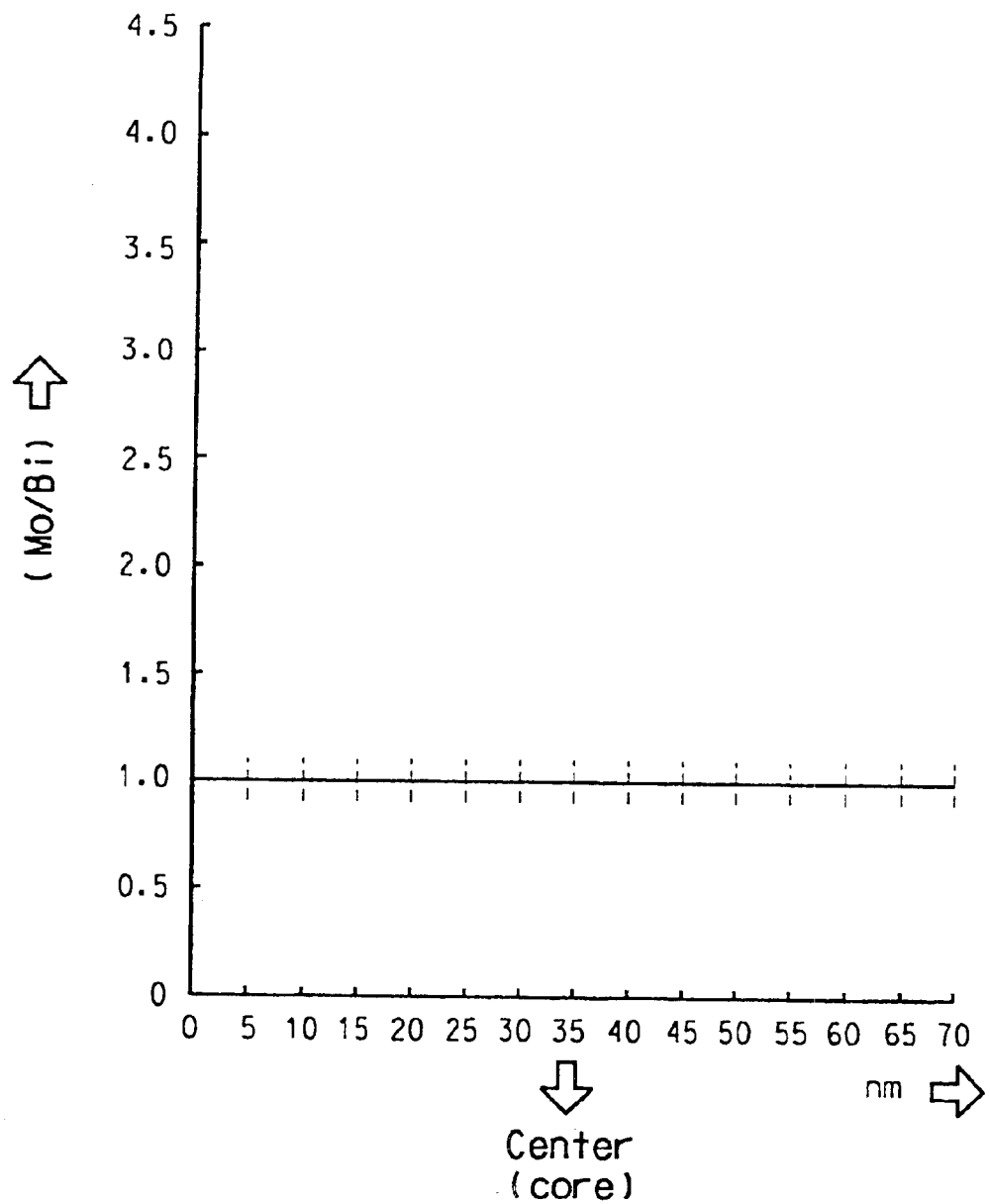
Figure 3A:
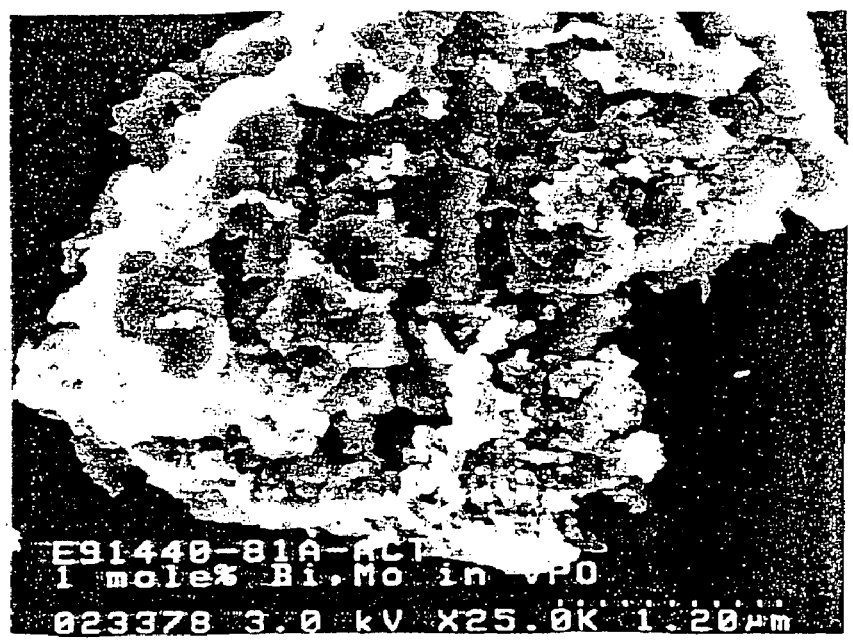
FIG. 3(*a*) shows the microstructure morphology of the promoter grafted (1 mol % Bi, Mo)VPO catalyst and FIG. 3(*b*) shows a qualitative compositional spectrum of the promoters in the structure. Catalyst contains catalyst crystals of variable sizes of up to 50 to 150 nanometer range and some in the 0.5 micrometer range.
Figure 3B:
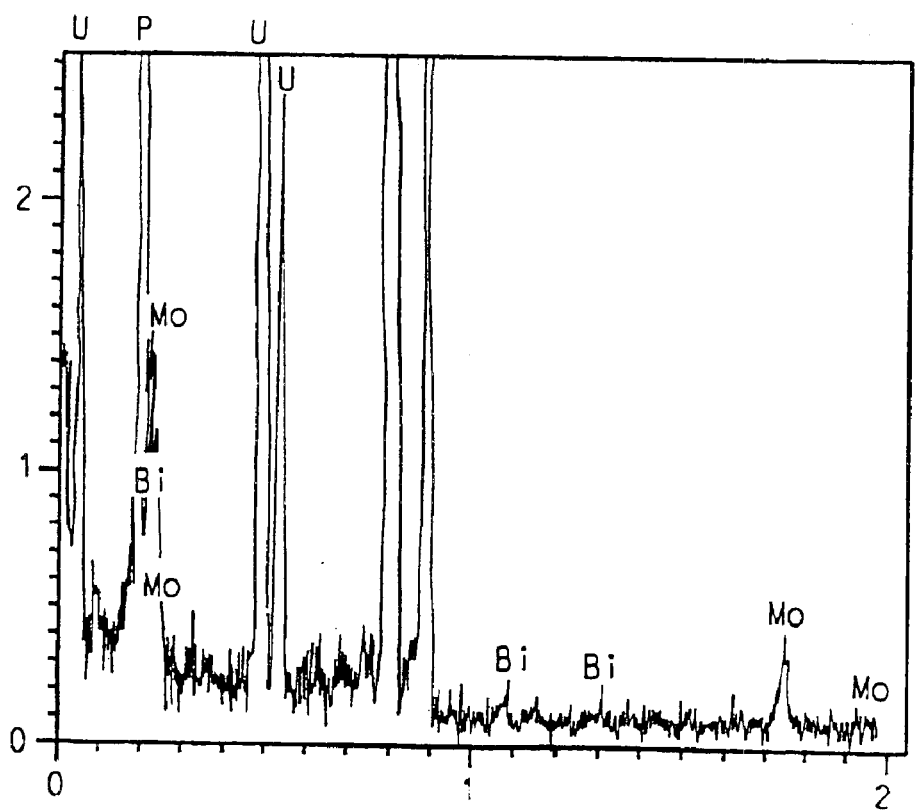

Morphologies of the surface and in the interior of the particles were also examined in the cross-sectioned samples. This promoter grafted catalyst composition is different from the calcined and activated (Bi, Mo) promoted VPO catalysts prepared by the coprecipitated method which did not show a compositional depth profile, with a Mo/Bi ratio of approximately 1 and (Mo/V ratio) of the surface=(Mo/ V) overall stoichiometry, shown in FIG. 2C.

EXAMPLES

Synthetic Procedures:

The general synthetic procedure for the catalysts of the present invention is listed under Example 1.

Example 1

1 Mole % Bi, Mo On Calsicat VOHPO$_4$.½H$_2$O

In an inert atmosphere nitrogen drybox, 1.872 g of BiCl$_3$ (Aldrich, 22, 438–9) was mixed with 1.6217 g of MoCl$_5$ (Alfa, 11832). The mixture was dissolved in 10 ml of ethanol (punctilious, Quantum Chemical). A blue-green solution was formed. In the inert atmosphere drybox, the liquid was added dropwise onto 100 g of preformed vanadium hydrogen phosphate precursor (Calsicat, E79517-119-1, unmilled commercial precursor). The material was dried under vacuum at 120° C. for five hours prior to activation.

The calcination/activation procedure generated the active phase by subjecting the precursor to the thermal conditions detailed below. In all cases, a small 3.5 cm fluidized bed was used, loaded with 20 g of catalyst. The calcination/activation protocol was as follows:

25–390° C. in air

390° C. 1 hour in air

390–460° C. 20 minutes in 1.5% butane/air

460° C. 18 hours in 1.5% butane/air

460–420° C. 1.5% butane/air

420–360° C. 1.5% butane/air

360–25° C. nitrogen

Example 2

1 Mole % Bi, Mo On Vanadium Phosphorus Oxide Precursor

The same synthetic procedure was used as described in Example 1. The precursor was dried under vacuum at 150° C. after impregnation with the bismuth and molybdenum containing solution, and was activated by the same procedure that was described in Example 1.

Comparative Example A

Ethanol On Vanadium Phosphorus Oxide Precursor 100 g of commercial VPO precursor (same starting VPO precursor as described in Example 1) was used. 10 ml of ethanol was added to the precursor. All subsequent steps, including activation, were identical to those described in Example 1.

Comparative Example A'

A VPO catalyst was made according to the procedure detailed in U.S. Pat. No. 3,864,280. This VPO catalyst by itself showed a k (sec$^{-1}$) of 0.50 and a selectivity at 40% conversion of 80.

Comparative Example B

HCl On VPO Precursor 100 g of commercial VPO precursor (same starting VPO precursor as described in Example 1) was used. 2.924 g HCl (37 wt %, EM Sciences. HX0603-4) was added to enough ethanol to prepare 10 ml of solution. The precursor was impregnated with the HCl/ethanol solution. The impregnation was performed in air, since inert atmosphere conditions were no longer needed. All subsequent steps, including the activation procedures, were identical to those described in Example 1.

Example 3

5 Mole % Bi, 5 Mole % Mo On VPO Precursor 7.13 g of bismuth trichloride was combined with 6.179 g of MoCl$_5$ and dissolved in 10 ml ethanol. 70 g of catalyst precursor was used in this preparation, and was unmilled commercial Calsicat (VOHPO$_4$.½H$_2$O). All subsequent steps, including the activation procedures, were identical to those described in Example 1.

Example 4

1 Mole % Bi, 1 Mole % Mo On VPO Precursor 1.3104 g of bismuth trichloride was combined with 1.135 g of MoCl$_5$ and dissolved in 35 ml ethanol. 70 g of catalyst precursor was used in this preparation, and was unmilled commercial Calsicat (VOHPO$_4$.½H$_2$O). All subsequent steps, including the activation procedures, were identical to those used in Example 1.

Example 5

$Bi_{0.05537}Mo_{0.003478}(VPO)_{0.9416}$, 5.537 Mole % Bi, 0.35 Mole % Mo On VPO precursor 7.55 g of bismuth trichloride was combined with 0.410 g of MoCl$_5$ in 10 ml of ethanol, and supported on 70 g of VPO precursor (Commercial Calsicat). All subsequent steps, including the activation procedures, were identical to those used in Example 1. Excess solvent was used in this Example.

Example 6

$Bi_{0.09788}Mo_{0.0492}(VPO)_{0.892}$

This composition is the limit of bismuth loading possible in ethanolic solution and incipient wetness. However, some MoCl$_5$ is needed for solution formation.

14.00 g of bismuth trichloride was combined with 0.610 g of MoCl$_5$ and dissolved in 12 ml ethanol. 70 g of catalyst precursor was used in this preparation, and was unmilled commercial Calsicat (VOHPO$_4$.½H$_2$O). All subsequent steps, including the activation procedures, were identical to those used in Example 1.

Example 7

5 Mole % Bi, 10 Mole % Mo On VPO Precursor 16.043 g of bismuth trichloride was combined with 13.902 g of MoCl$_5$ and dissolved in 10 ml ethanol. 70 g of catalyst precursor was used in this preparation, and was unmilled commercial Calsicat (VOHPO$_4$.½H$_2$O). All subsequent steps, including the activation procedures, were identical to those used in Example 1.

Comparative Example C

1 Mole % Bi, 1 Mole % Mo On VPO Precursor; Aqueous Impregnation with Bi(NO$_3$)$_3$.5 H$_2$O 2.015 g of bismuth nitrate (Bi(NO$_3$)$_3$.5 H$_2$O) was dissolved in 8 ml H$_2$O and 4 ml 70% nitric acid. 0.7335 g of ammonium molybdate, $(NH_4)_6Mo_7O_{24} \cdot 4H_2O$ was added and dissolved in this solution. 70 g of catalyst precursor was used in this preparation, and was unmilled commercial Calsicat $(VOHPO_4 \cdot \frac{1}{2}H_2O)$. All subsequent steps, including the activation procedures, were identical to those used in Example 1. This demonstrated that a conventional and aqueous impregnation of the VPO precursor did not result in an improved catalyst.

Example 8

5 Mole % Mo On VPO Precursor 5.853 g of $MoCl_5$ and dissolved in 7 ml ethanol. 70 g of catalyst precursor was used in this preparation, and was unmilled commercial Calsicat $(VOHPO_4 \cdot \frac{1}{2}H_2O)$. All subsequent steps, including the activation procedures, were identical to those described in Example 1.

Example 9

1 Mole % Mo On VPO Precursor 1.1234 g of $MoCl_5$ was dissolved in 7 ml ethanol. 70 g of catalyst precursor was used in this preparation, and was unmilled commercial Calsicat $(VOHPO_4 \cdot \frac{1}{2}H_2O)$. All subsequent steps, including the activation procedures, were identical to those described in Example 1.

Example 10

2.5 Mole % Bi and 2.5 Mole % Mo On VPO Precursor 3.378 g of $BiCl_3$ and 2.9267 g of $MoCl_5$ was dissolved in 14 ml ethanol. 70 g of catalyst precursor was used in this preparation, and was unmilled commercial Calsicat $(VOHPO_4 \cdot \frac{1}{2}H_2O)$. All subsequent steps, including the activation procedures, were identical to those described in Example 1.

Comparative Example D

A VPO catalyst was made according to the procedure detailed in U.S. Pat. No. 3,864,280. This VPO catalyst by itself showed a k (sec-1) of 0.50 and a selectivity at 40% conversion of 80.

Comparative Examples E, F, G and H are shown in Table 2 below.

Example 11

5.54 Mole % Bi and 0.35 Mole % Mo On VPO Precursor 7.549 g of $BiCl_3$ and 0.4108 g of $MoCl_5$ was dissolved in 12 ml ethanol. 70 g of catalyst precursor was used in this preparation, and was unmilled commercial Calsicat $(VOHPO_4 \cdot \frac{1}{2}H_2O)$. All subsequent steps, including the activation procedures, were identical to those described in Example 1.

Reactor Data:

The items contained in the examples above were tested on the micro-reactor as described above. The results are summarized below in Table 1.

TABLE 1

Micro-Reactor Data using Bi and Mo Alkoxides Grafted on Pre-Formed Commercial Vanadium Phosphate Supports: Effects of Loading and Bi/Mo Ratio

| | 2% butane air. 380° C. | |
| --- | --- | --- |
| Example No. | k (sec$^{-1}$) | sel. @ 40% conv. |
| 1 | 0.90 | 87 |
| 2 | 0.88 | 83 |
| Comp. A | 0.59 | 81 |
| Comp. A' | 0.50 | 80 |
| Comp. B | 0.49 | 83 |
| 3 | 0.89 | 66 |
| 4 | 1.12 | 87 |
| 5 | 1.84 | 62 |
| 6 | 1.22 | 71 |
| 7 | 0.92 | 63 |
| Comp. C | 0.37 | 69 |
| 8 | 1.22 | 71 |
| 9 | 0.91 | 90 |
| 10 | 1.61 | 83 |
| 11 | 1.96 | 78 |

Other Metal Promoter Ions with Molybdenum:

A procedure identical to that described in Example 1 above was followed for Compariative Examples D–F and Examples 12–17 below. EtOH represents ethanol.

TABLE 2

| Example No. | Composition | Micro-ReactorDATA, 380° C., 2% butane/air | | promoter precursor | supplier and catalogue no. | amount (g) | promoter precursor | supplier and catalogue no. | amount (g) |
| --- | --- | --- | --- | --- | --- | --- | --- | --- | --- |
| | | k (sec$^{-1}$) | sel at 40% conversion | | | | | | |
| Comp. D | VPO standard | 0.5 | 80 | 70 g | | | | | |
| 12 | $(Mn_{0.01}Mo_{0.01})(VPO)_{0.98}$ | 1.13 | 85 | 70 g $MnCl_2$ anhydrous | Johnson Matthey 11868 | 0.5228 g | 7 ml EtOH total | $MoCl_5$ Alfa, 11832 | 1.135 g |
| 13 | $(Zn_{0.01}Mo_{0.01})(VPO)_{0.98}$ | 1.07 | 83 | 70 g $ZnCl_2$ | Baker, lot A47331 | 0.5663 g | 7 ml EtOH total | $MoCl_5$ Alfa, 11832 | 1.135 g |
| 14 | $(Ni_{0.01}Mo_{0.01})(VPO)_{0.98}$ | 0.98 | 87 | 70 g $NiCl_2 \cdot 6H_2O$ | Aldich, 22,338-7 | 0.9876 g | 7 ml EtOH total | $MoCl_5$ Alfa, 11832 | 1.135 g |
| 15 | $(Sn_{0.01}Mo_{0.01})(VPO)_{0.98}$ | 1.48 | 84 | 70 g $SnCl_2$, anhydrous | Alfa 11535 | 0.7876 | 7 ml EtOH total | $MoCl_5$ Alfa, 11832 | 1.135 g |
| 16 | $(Fe_{0.01}Mo_{0.01})(VPO)_{0.98}$ | 1.26 | 85 | 70g $FeCl_3$, anhydrous | Alfa 12357 | 0.6739 g | 7 ml EtOH total | $MoCl_5$ Alfa, 11832 | 1.135 g |
| 17 | $(Co_{0.01}Mo_{0.01})(VPO)_{0.98}$ | 0.96 | 85 | 70 g $CoCl_2$ anhydrous | Alfa 12303, lot HO2G19 | 0.5394 | 10 ml total EtOH | $MoCl_5$ Alfa, 11832 | 1.135 g |

Promoter Grafting On Pre-Formed, Spray Dried Precursor (Contains 10 wt % $SiO_2$)

The procedure as described above in Example 1 was followed for the following examples. The VPO precursor was spray dried with polysilicic acid for attrition resistance (as described in U.S. Pat. No. 4,769,477). The quantities of the VPO/$SiO_2$ precursor, reagents, and reagent descriptions are as indicated in the table below. (The VPO control samples, as indicated by the Comparative Examples shown as "Comp", are controls for those samples that directly follow in the table below.)

TABLE 3

| Example No. | Composition | k (sec$^{-1}$) | sel at 40% conversion | g VPO/$SiO_2$ precursor | promoter precursor | supplier and catalogue no. |
|---|---|---|---|---|---|---|
| Comp. E | VPO/$SiO_2$ control | 0.64 | 75 | | | |
| 18 | $(Ti_{0.107}Mo_{0.107})(VPO/SiO_2)_{0.9786}$ | 1.06 | 82 | 1,000 g | $TiCl_4$ anhydrous | Aldrich, 25431-2 |
| 19 | $(Ti_{0.107}Mo_{0.107})(VPO/SiO_2)_{0.9786}$ | 1.14 | 84 | 1,000 g | $TiCl_4$ anhydrous | Aldrich, 25431-2 |
| 20 | $(Zr_{0.01}Mo_{0.01})(VPO/SiO_2)_{0.98}$ | 0.89 | 86 | 70 g | $ZrOCl_2$, zirconyl chloride | Pfaltz and Bauer, Z01565 |
| Comp. F | VPO/$SiO_2$ control | 0.64 | 75 | | | |
| 21 | $(Ti_{0.01}Mo_{0.01})(VPO/SiO_2)_{0.98}$ | 0.93 | 83 | 70 g | $TiCl_4$ anhydrous | Aldrich, 25431-2 |
| 22 | $(Zr_{0.01}Mo_{0.01})(VPO/SiO_2)_{0.98}$ | 1.01 | 85 | 70 g | $ZrOCl_2$, zirconyl chloride | Pfaltz and Bauer, Z01565 |
| Comp. G | VPO/$SiO_2$ control | 0.77 | 86 | | | |
| 23 | $(Ti_{0.01}Mo_{0.01})(VPO/SiO_2)_{0.98}$ | 1.2 | 86 | | | |
| Comp. H | VPO/$SiO_2$ control | 0.62 | 81 | | | |
| 24 | $(Ti_{0.01}Mo_{0.01})(VPO/SiO_2)_{0.98}$ | 1.23 | 85 | 70 g | $TiCl_4$ anhydrous | Aldrich, 25431-2 |
| 25 | $(Cu_{0.01}Mo_{0.01})(VPO/SiO_2)_{0.98}$ | 0.99 | 86 | 70 g | $CuCl_2$ anhydrous | Alfa 12457 |
| 26 | $(Al_{0.01}Mo_{0.01})(VPO/SiO_2)_{0.98}$ | 0.96 | 84 | 70 g | $AlCl_3$, anhydrous | EM Sciences |
| 27 | $(Fe_{0.01}Mo_{0.01})(VPO/SiO_2)_{0.98}$ | 0.95 | 85 | 70 g | $FeCl_3$, anhydrous | Alfa 12357 |
| 28 | $(Sn_{0.01}Mo_{0.01})(VPO/SiO_2)_{0.98}$ | 1.08 | 84 | 70 g | $SnCl_2$, anhdrous | Alfa 11535 |
| 29 | $(Zr_{0.01}Mo_{0.01})(VPO/SiO_2)_{0.98}$ | 0.96 | 86 | 70 g | $ZrOCl_2$ | Pfaltz and Bauer, Z01565 |
| 30 | $(Sb_{0.01}Mo_{0.01})(VPO/SiO_2)_{0.98}$ | 0.9 | 80 | 70 g | $SbCl_5$ | Johnson and Matthey, 17570, lot C18C19 |

| Example No. | amount (g) | solvent used | promoter precursor | supplier and catalogue no. | amount (g) |
|---|---|---|---|---|---|
| Comp. E | | | | | |
| 18 | 10.8583 g | 100 ml EtOH total for all promoters | $MoCl_5$ | Alfa, 11832 | 15.636 g |
| 19 | 10.8583 g | 100 ml EtOH total for all promoters | $MoCl_5$ | Alfa, 11832 | 15.636 g |
| 20 | 0.6660 g | Total 7 ml EtOH for both promoters | $MoCl_5$ | Alfa, 11832 | 1.0214 g |
| Comp. F | | | | | |
| 21 | 0.7092 g | 7 ml EtOH for all promoters | $MoCl_5$ | Alfa, 11832 | 1.0214 g |
| 22 | 0.6660 g | total 7 ml EtOH for both promoters | $MoCl_5$ | Alfa, 11832 | 1.0214 g |
| Comp. G | | | | | |
| 23 | | | | | |
| Comp. H | | | | | |
| 24 | 0.7092 | 7 ml, total | $MoCl_5$ | Alfa, 11832 | 1.0214 |

TABLE 3-continued

| 25 | 0.5027 g | 7 ml, total EtOH | MoCl$_5$ | Alfa, 11832 | 1.0214 |
| 26 | 0.4986 g | 7 ml, total EtOH | MoCl$_5$ | Alfa, 11832 | 1.0214 |
| 27 | 0.6064 | 7 ml, total EtOH | MoCl$_5$ | Alfa, 11832 | 1.0214 |
| 28 | 0.7089 g | 7 ml, total EtOH | MoCl$_5$ | Alfa, 11832 | 1.0214 |
| 29 | 0.660 g | 7 ml, total EtOH | MoCl$_5$ | Alfa, 11832 | 1.0214 |
| 30 | 1.1180 g | 7 ml, total EtOH | MoCl$_5$ | Alfa, 11832 | 1.0214 |

What is claimed is:

1. A method for enhancing the activity of a vanadium phosphorus oxide catalyst comprising grafting onto or otherwise reacting one or more-promoter reagents with a catalyst to produce a catalyst composition with a promoter rich surface and wherein said composition is exposed to a heating cycle to form a promoted catalyst, wherein said promoter reagents comprise molybdenum alkoxide, molybdenum chloride or combinations thereof, and a second promoter reagent selected from the group consisting of alkoxides, anhydrous chlorides, carbonyls and organometallic complexes of A;

wherein A is selected from the group consisting of Mn, Zn, Ni, Sn, Fe, Co, Ti, Zr, Bi, Al, Cu, Sb, or combinations thereof in amounts expressed by the formula $[Mo_{1-x}A_x]_yD$, wherein $0 \leq x < 1$ and $0.01 \leq y \leq 0.4$, and the atomic ratio of Mo to V (Mo/V) is greater than or equal to about 0.01;

wherein D represents vanadium, vanadium phosphorus oxide catalyst or vanadium phosphorus oxide catalyst with binder included therein.

2. The method of claim 1 wherein the promoter-comprises Mo alkoxide or Mo chloride, or combinations thereof.

3. The method of claim 3 wherein Mo is grafted onto or reacted with the catalyst surface so that the surface density of Mo is greater than the density of Mo in the non-surface area of the catalyst.

4. The method of claim 4 wherein the ratio of molybdenum to vanadium on the surface of the catalyst to molybdenum to vanadium in the overall bulk of the catalyst is represented by the equation (Mo/V) Surface $\geq 1.10$ (Mo/V) overall bulk.

5. The method of claim 1 wherein $0 \leq x \leq 0.75$ and $0.01 \leq y \leq 0.05$.

6. The method of claim 7 wherein the catalyst additionally comprises a binder and the binder is $SiO_2$.

7. A promoted vanadium phosphorus oxide catalyst composition comprising vanadium phosphorus oxide and a promoter wherein the promoter comprises molybdenum, or molybdenum in combination with A. and wherein $[Mo_{1-x}A_x]_yD$ wherein $0 < x < 1$ and $0.001 < y < 0.4$, and the atomic ratio of Mo to V (Mo/V) is greater than or equal to about 0.01; wherein D represents vanadium, vanadium phosphorus oxide catalyst or vanadium phosphorus oxide catalyst and wherein A is selected from the group consisting of Mn, Zn, Ni, Sb Fe, Co, Ti, Zr, Bi, Al, Cu, or combinations thereof; and the surface density of Mo is greater than the density of Mo in the non-surface area of the catalyst.

8. The catalyst composition of claim 7 wherein the promoter comprises Mo.

9. The catalyst composition of claim 8 wherein the ratio of molybdenum to vanadium on the surface of the catalyst to molybdenum to vanadium in the overall bulk of the catalyst is represented by the equation (Mo/V) Surface $\geq 1.10$ (Mo/V) overall bulk.

10. The catalyst composition of claim 12 wherein $0 \leq x \leq 0.75$ and $0.01 \leq y \leq 0.05$.

* * * * *